US008299215B2

(12) United States Patent
Davidson et al.

(10) Patent No.: US 8,299,215 B2
(45) Date of Patent: Oct. 30, 2012

(54) METHODS AND COMPOSITIONS FOR TREATING BRAIN DISEASES

(75) Inventors: Beverly L. Davidson, North Liberty, IA (US); Yong Hong Chen, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 1055 days.

(21) Appl. No.: 12/172,121

(22) Filed: Jul. 11, 2008

(65) Prior Publication Data

US 2009/0162332 A1 Jun. 25, 2009

Related U.S. Application Data

(60) Provisional application No. 60/959,638, filed on Jul. 14, 2007.

(51) Int. Cl.
*A61K 38/04* (2006.01)
*A61K 48/00* (2006.01)
*C12N 7/01* (2006.01)

(52) U.S. Cl. ............... 530/329; 424/93.2; 435/235.1
(58) Field of Classification Search ............... None
See application file for complete search history.

(56) References Cited

U.S. PATENT DOCUMENTS

| 6,468,524 | B1 | 10/2002 | Chiorini et al. | |
| 2004/0258666 | A1 | 12/2004 | Passini et al. | |
| 2005/0287122 | A1* | 12/2005 | Bartlett et al. | 424/93.2 |
| 2006/0286545 | A1* | 12/2006 | Weber et al. | 435/5 |

FOREIGN PATENT DOCUMENTS

WO   WO 2005/005610 A2   1/2005

OTHER PUBLICATIONS

Work, L. et al., "Vascular Bed-Targeted in Vivo Gene Delivery Using Tropism-Modified Adeno-associated Viruses", Jan. 2006, Mol. Ther., vol. 13: pp. 683-693.*

Berns, "Parvoviridae and their replication", *Virology*, 2, (62), pp. 1743-1763, 1990.

Brenz Verca, S., Examiner, Extended European Search Report for European Application No. 08781733.4, 11 pages, dated May 10, 2011.

Buning et al., "Receptor targeting of adeno-associated virus vectors", *Gene. Ther.*, vol. 10, pp. 1142-1151, 2003.

Chen et al., "Molecular of Disease Brain Endothelia Provide new Sites for CNHS-directed Enzyme Therapy", *Nature Medicine*, vol. 15, No. 10, pp. 1215-1218, including one supplemental page, 2009.

Davidson et al., "Recombinant adeno-associated virus type 2, 4, and 5 vectors: Transduction of variant cell types and regions in the mammalian central nervous system", *PNAS*, vol. 97, No. 7, pp. 3428-3432, 2000.

Kotin, "Prospects for the use of adeno-associated virus as a vector for human gene therapy", *Human Gene Therapy*, 5, pp. 793-801, including 4 supplemental pages, 1994.

Liu et al., "A novel peptide defined through phage display for therapeutic protein and vector neuronal targeting", *Neurobiology of Disease*, vol. 19, pp. 407-418, 2005.

Liu et al., "Functional Correction of CNS Phenotypes in a Lysosomal Storage Disease Model Using Adeno-Associated Virus Type 4 Vectors", *J. Neurosci 25*, (41), pp. 9321-9327, 2005.

Nicklin et al., "Efficient and selective AAV2-mediated gene transfer directed to human vascular endothelial cells", *Mol Ther.* vol. 4, No. 2, pp. 174-181, 2001.

Patent Cooperation Treaty, International Searching Authority, Written Opinion and International Search Report for PCT/US2008/069866, 13 pages, dated Mar. 13, 2009.

White et al., "Targeted gene delivery to vascular tissue in vivo by tropism-modified adeno-associated virus vectors", *Circulation*, vol. 109, pp. 513-519, 2004.

Work et al., "Vascular Bed-Targeted in Vivo Gene Delivery Using Tropism-Modified Adeno-associated Viruses", *Molecular Therapy* vol. 13, No. 4, pp. 683-693, 2006.

* cited by examiner

*Primary Examiner* — Michael Burkhart
(74) *Attorney, Agent, or Firm* — Viksnins Harris & Padys PLLP

(57) ABSTRACT

The present disclosure provides targeting peptides and vectors containing a sequence that encodes targeting peptides that deliver agents to the brain.

9 Claims, 8 Drawing Sheets

| Group 1 PxxPS (8) SEQ ID NO:1 | Group 2 SPxxP (4) SEQ ID NO:2 | Group 3 TLH (5) SEQ ID NO:3 | Group 4 QSxY (2) SEQ ID NO:4 |
|---|---|---|---|
| PYFPSLS (2) SEQ ID NO:5 | SPPLPPK SEQ ID NO:12 | GWTLHNK(3) SEQ ID NO:16 | QSFYILT SEQ ID NO:19 |
| YAPLTPS SEQ ID NO:6 | SPKPPPG SEQ ID NO:13 | KIPPTLH SEQ ID NO:17 | TTQSEYG SEQ ID NO:20 |
| PLSPSAY SEQ ID NO:7 | NWSPWDP SEQ ID NO:14 | ISQTLHG SEQ ID NO:18 | |
| DSPAHPS SEQ ID NO:8 | DSPAHPS SEQ ID NO:15 | | |
| GTPTHPS SEQ ID NO:9 | | | |
| PDAPSNH SEQ ID NO:10 | | | |
| TEPHWPS SEQ ID NO:11 | | | |

Fig. 2A

| Group 1<br>LxSS (7)<br>SEQ ID NO:21 | Group 2<br>PFxG (5)<br>SEQ ID NO:22 | Group 3<br>SIxA (3)<br>SEQ ID NO:23 |
|---|---|---|
| MLVSSPA<br>SEQ ID NO:24<br>LPSSLQK (2)<br>SEQ ID NO:25<br>PPLLKSS (2)<br>SEQ ID NO:26<br>PXKLDSS<br>SEQ ID NO:27<br>AWTLASS<br>SEQ ID NO:28 | WPFYGTP(3)<br>SEQ ID NO:29<br>GTFPFLG<br>SEQ ID NO:30<br>GQVPFMG<br>SEQ ID NO:31 | ANFSILA<br>SEQ ID NO:32<br>GSIWAPA<br>SEQ ID NO:33<br>SIAASFS<br>SEQ ID NO:34 |

Fig. 2B

Fig. 5A
CLN2-/- Mouse
| Peptide | Viral Titer |
|---|---|
| ARMFANMG | $1.76 \times 10^{12}$ |
Fig. 5B
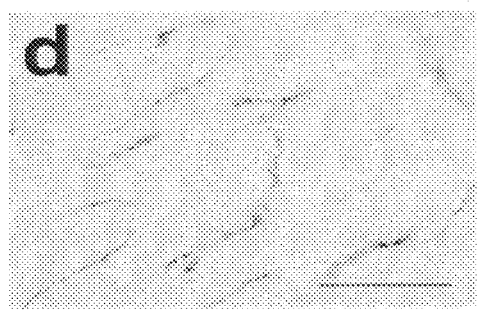
Fig. 5C
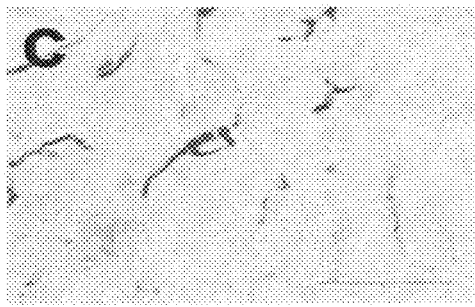
Fig. 5D
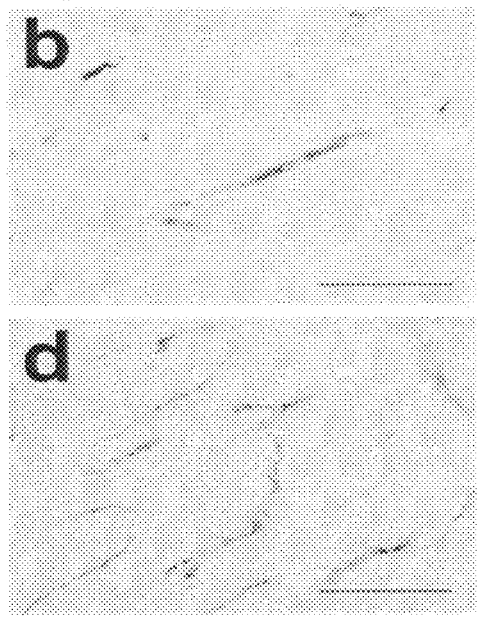
Fig. 5E
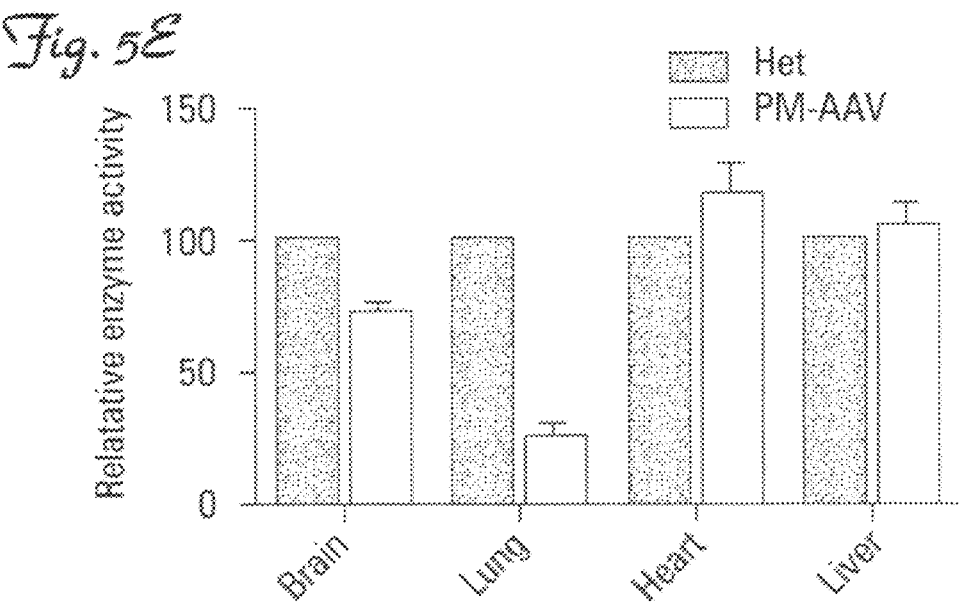

METHODS AND COMPOSITIONS FOR TREATING BRAIN DISEASES

RELATED APPLICATION

This application claims priority to U.S. Provisional Patent Application No. 60/959,638, filed Jul. 14, 2007, the entirety of which is incorporated herein by reference.

FEDERAL GRANT SUPPORT

Portions of the present invention were made with support of the United States Government via a grant from the National Institutes of Health under grant number HD33531. The government has certain rights in the invention.

BACKGROUND

Gene transfer is now widely recognized as a powerful tool for analysis of biological events and disease processes at both the cellular and molecular level. More recently, the application of gene therapy for the treatment of human diseases, either inherited (e.g., ADA deficiency) or acquired (e.g., cancer or infectious disease), has received considerable attention. With the advent of improved gene transfer techniques and the identification of an ever expanding library of defective gene-related diseases, gene therapy has rapidly evolved from a treatment theory to a practical reality.

Traditionally, gene therapy has been defined as a procedure in which an exogenous gene is introduced into the cells of a patient in order to correct an inborn genetic error. Although more than 4500 human diseases are currently classified as genetic, specific mutations in the human genome have been identified for relatively few of these diseases. Until recently, these rare genetic diseases represented the exclusive targets of gene therapy efforts. Accordingly, most of the NIH approved gene therapy protocols to date have been directed toward the introduction of a functional copy of a defective gene into the somatic cells of an individual having a known inborn genetic error. Only recently, have researchers and clinicians begun to appreciate that most human cancers, certain forms of cardiovascular disease, and many degenerative diseases also have important genetic components, and for the purposes of designing novel gene therapies, should be considered "genetic disorders." Therefore, gene therapy has more recently been broadly defined as the correction of a disease phenotype through the introduction of new genetic information into the affected organism.

In in vivo gene therapy, a transferred gene is introduced into cells of the recipient organism in situ that is, within the recipient. In vivo gene therapy has been examined in several animal models. Several recent publications have reported the feasibility of direct gene transfer in situ into organs and tissues such as muscle, hematopoietic stem cells, the arterial wall, the nervous system, and lung. Direct injection of DNA into skeletal muscle, heart muscle and injection of DNA-lipid complexes into the vasculature also has been reported to yield a detectable expression level of the inserted gene product(s) in vivo.

Treatment of diseases of the central nervous system, e.g., inherited genetic diseases of the brain, remains an intractable problem. Examples of such are the lysosomal storage diseases. Collectively, the incidence of lysosomal storage diseases (LSD) is 1 in 10,000 births world wide, and in 65% of cases, there is significant central nervous system (CNS) involvement. Proteins deficient in these disorders, when delivered intravenously, do not cross the blood-brain barrier, or, when delivered directly to the brain, are not widely distributed. Thus, therapies for the CNS deficits need to be developed.

SUMMARY

The present inventors have discovered peptides that function to target agents, such as viral vectors, to vascular endothelial cells of the central nervous system. The present disclosure describes a method to utilize these novel peptides to redirect, for example, viral capsids to the cell type of interest. In this instance, endothelial cells lining brain blood vessels are targeted by the identified peptides. Vectors harboring capsid proteins modified to include such peptides can be used to provide therapeutic agents to the central nervous system (e.g., the brain).

As used herein, the term "targets" means that the capsid protein of a virus, such as an adeno-associated virus (AAV), preferentially binds to one type of tissue (e.g., liver tissue) over another type of tissue (e.g., brain tissue), and/or binds to a tissue in a certain state (e.g., wildtype or diseased). In certain embodiments, the genetically modified capsid protein may "target" brain vascular epithelia tissue by binding at level of 10% to 1000% higher than a comparable, unmodified capsid protein. For example, an AAV having a genetically-modified capsid protein may bind to brain vascular epithelia tissue at a level 50% to 100% greater than an unmodified AAV virus. In certain embodiments, the nucleic acids encoding the capsid proteins of a virus are modified such that the viral capsids preferentially bind to brain vascular endothelium in a mammal suffering from lysosomal storage disease, or, using different sequences, to wildtype brain vascular endothelium in brain of the same species.

The present invention provides a modified adeno-associated virus (AAV) capsid protein containing a targeting peptide, wherein the targeting peptide is from 3 to 10 amino acids in length and wherein the targeting peptide targets an AAV to brain vascular endothelium. In certain embodiments, the targeting peptide is 3, 4, 5, 6 or 7 amino acids in length. In certain embodiments, the AAV is AAV2, although the tropism is modified so it would follow that such modifications would change the tropism of any AAV.

In certain embodiments, the targeting peptide targets wildtype brain vascular endothelium. In certain embodiments, the targeting peptide is PXXPS (SEQ ID NO:1), SPXXP (SEQ ID NO:2), TLH (SEQ ID NO:3), or QSXY (SEQ ID NO:4), as expressed in an amino to carboxy orientation or in a carboxy to amino orientation. In certain embodiments, the targeting peptide is PYFPSLS (SEQ ID NO:5), YAPLTPS (SEQ ID NO:6), PLSPSAY (SEQ ID NO:7), DSPAHPS (SEQ ID NO:8), GTPTHPS (SEQ ID NO:9), PDAPSNH (SEQ ID NO:10), TEPHWPS (SEQ ID NO:11), SPPLPPK (SEQ ID NO:12), SPKPPPG (SEQ ID NO:13), NWSPWDP (SEQ ID NO:14), DSPAHPS (SEQ ID NO:15), GWTLHNK (SEQ ID NO:16), KIPPTLH (SEQ ID NO:17), ISQTLHG (SEQ ID NO:18), QSFYILT (SEQ ID NO:19), or TTQSEYG (SEQ ID NO:20), as expressed in an amino to carboxy orientation or in a carboxy to amino orientation. It should be noted that the orientation of the sequence is not important. For example, the peptide may be oriented from the amino-terminal end to carboxy-terminal end of the peptide to be TTQSEYG (SEQ ID NO:20) or may be from the amino-terminal end to carboxy-terminal end of the peptide to be GYESQTT (SEQ ID NO:42).

In certain embodiments, the targeting peptide targets a diseased brain vascular endothelium. In certain embodiments, the targeting peptide targets brain vascular endothelium in a subject that has a lysosomal storage disease. In certain embodiments, the targeting peptide targets a mucopolysaccharide (MPS) VII brain vascular endothelium. In certain embodiments, the targeting peptide is LXSS (SEQ ID NO:21), PFXG (SEQ ID NO:22), or SIXA (SEQ ID NO:23), as expressed in an amino to carboxy orientation or in a carboxy to amino orientation. In certain embodiments, the targeting peptide is MLVSSPA (SEQ ID NO:24), LPSSLQK (SEQ ID NO:25), PPLLKSS (SEQ ID NO:26), PXKLDSS (SEQ ID NO:27), AWTLASS (SEQ ID NO:28), WPFYGTP (SEQ ID NO:29), GTFPFLG (SEQ ID NO:30), GQVPFMG (SEQ ID NO:31), ANFSILA (SEQ ID NO:32), GSIWAPA (SEQ ID NO:33), or SIAASFS (SEQ ID NO:34), as expressed in an amino to carboxy orientation or in a carboxy to amino orientation.

In certain embodiments, targeting peptide targets TPP1-deficient-brain vascular endothelium. In certain embodiments, the targeting peptide is GMNAFRA (SEQ ID NO:41), as expressed in an amino to carboxy orientation or in a carboxy to amino orientation.

The present invention provides a nucleic acid sequence encoding a modified capsid described hereinabove.

The present invention provides an AAV virus containing the capsid protein modified genetically to encode the peptides described hereinabove.

The present invention provides a viral vector comprising a nucleic acid encoding the capsid protein as described hereinabove. In certain embodiments, the viral vector further contains a nucleic acid sequence encoding a nucleic acid of interest. In certain embodiments, the nucleic acid of interest is a therapeutic agent. In certain embodiments, the therapeutic agent is an enzyme or an RNAi molecule (e.g., siRNA, shRNA or miRNA molecules). In certain embodiments, the therapeutic agent is β-glucuronidase or tripeptidyl protease.

The present invention provides a cell containing the viral vector described hereinabove.

The present invention provides a cell transduced by the viral vector described hereinabove. In certain embodiments, the cell is a mammalian cell. In certain embodiments, the cell is a human cell. In other embodiments, the cell is a non-human cell. In certain embodiments, the cell is in vitro, and in other embodiments, the cell is in vivo. In certain embodiments, the cell is an endothelial cell. In certain embodiments, the cell is a vascular endothelial cell.

The present invention provides a method of treating the brain disease in a mammal by administering the viral vector described hereinabove or the cell described hereinabove to the mammal. In certain embodiments, the mammal is human. In certain embodiments, the disease is a lysosomal storage disease (LSD), such as infantile or late infantile ceroid lipofuscinoses, neuronopathic Gaucher, Juvenile Batten, Fabry, MLD, Sanfilippo A, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease. In certain embodiments, the disease is a neurodegenerative disease, such as Huntington's disease, ALS, hereditary spastic hemiplegia, primary lateral sclerosis, spinal muscular atrophy, Kennedy's disease, Alzheimer's disease, a polyglutamine repeat disease, or Parkinson's disease.

The present invention provides a method to deliver an agent to the central nervous system of a subject, by transducing vascular endothelial cells with a viral vector described hereinabove so that the transduced vascular endothelial cells express the therapeutic agent and deliver the agent to the central nervous system of the subject. In certain embodiments, the viral vector transduces vascular endothelial cells The present invention provides a viral vector as described hereinabove for use in medical treatment or diagnosis.

The present invention provides a use of the viral vector described hereinabove to prepare a medicament useful for treating a lysosomal storage disease in a mammal.

The present invention provides a cell as described hereinabove for use in medical treatment or diagnosis.

The present invention provides a use of the cell as described hereinabove to prepare a medicament useful for treating a lysosomal storage disease in a mammal.

The present invention provides a method for identifying peptides that target brain vascular endothelium by using phage display biopanning so as to identify such peptides.

BRIEF DESCRIPTION OF THE DRAWINGS

FIG. 1A depicts a vascular cast of the human brain, and 1B shows four cells of the CNS microvasculature.

FIGS. 2A-2D. In vivo phage display panning to identify peptide motifs with high affinity for cerebral vasculature. (FIG. 2A, 2B) After 5 rounds of in vivo phage display panning, phage with distinct peptide motifs were identified from wildtype (a) and MPS VII (b) mice. (FIGS. 2C, 2D) Selected phage were individually injected via tail vein, and phage was recovered and tittered from cerebral vasculature of wildtype (c) (SEQ ID NOS 5-14, 16-18, 20 and 19, respectively in order of appearance) and MPS VII (d) mice (SEQ ID NOS 29-31, 26, 34, 28, 25, 27, 33, 32 and 24, respectively in order of appearance). Data presented as mean±SEM.

(FIGS. 3A, 3B) Four weeks after tail vein injection of peptide-modified virus ($1.0 \times 10^{11}$ genome particles/mouse), viral genomes were quantified by RT-PCR in brain and liver of wildtype (a) and MPS VII (b) mice.

(FIGS. 4A-4H) Toluidine-blue stained sections (1 µm) through cerebral cortex (ctx), hippocampus (hc), striatum (str), and cerebellum (cb) of MPS VII mice injected via tail vein with either AAV-WT or AAV-PFG expressing β-glucuronidase. Representative images are shown. (FIG. 4I) In the context fear conditioning assay, MPS VII mice treated with AAV-WT control virus (n=4), MPS VII mice treated with AAV-PFG (n=6), and heterozygous controls (n=6) were tested for their ability to discriminate a harmful vs benign context (see methods). Decreases in freezing time corresponds to intact context discrimination. Data presented as mean±SEM, *$p<0.05$. (FIG. 4J) Binding of AAV-PFG to cerebral vasculature requires chondroitin sulfate. Purified brain vasculatures from wildtype (WT) or MPS VII (MPS) mice were pre-incubated with PBS alone, PNGase (100 U/reaction), or chondroitinase ABC (2 U/reaction). Vasculatures were then incubated with wildtype AAV or AAV-PFG ($1.0 \times 10^{11}$ genome particles) in 500 µl PBS. Bound viral particles were quantified by RT-PCR. Data presented as mean±SEM. (FIG. 4K) Binding of AAV-PFG to purified brain vasculature from MPS VII mice in the presence or absence of 2 mg/ml chondroitin sulfate. Data presented as mean±SEM.

FIGS. 5A-5E. In vivo phage display panning in TPP1-deficient (CLN2 −/−) mice. (FIG. 5A) After 5 rounds of panning, a single peptide was recovered—ARFANMG (SEQ ID NO: 43). AAV modified with this peptide was tittered at $1.76 \times 10^{12}$ viral genomes/ml. (FIGS. 5B-5D) Immunostaining for TPP1 3 weeks after tail vein injection of modified virus (1.76×10$^{11}$ viral genomes) into TPP1-deficient mice reveals enzyme in cerebral cortex (b), midbrain (c), and cerebellum (d). Scale bars, 50 μm. (FIG. 5E) In vitro assay for TPP1 activity in several tissues following tail vein injection of peptide modified virus. Activity levels expressed relative to heterozygous control.

DETAILED DESCRIPTION

Figure 1A:
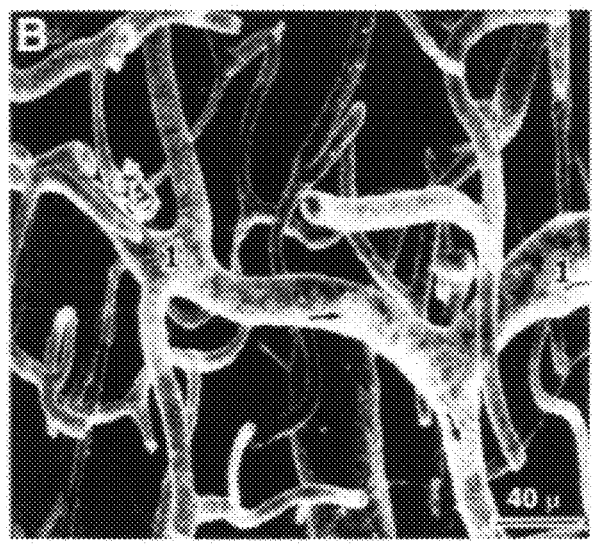
FIGS. 1A and 1B.

Certain embodiments of the present disclosure provide a viral vector comprising a modified capsid, wherein the modified capsid comprises at least one amino acid sequence that targets the viral vector to brain vascular endothelium.

In certain embodiments, the viral vector is an adeno associated viral vector (AAV). In certain embodiments, the AAV is AAV2.

In certain embodiments, the amino acid sequence that targets brain vascular endothelium comprises or consists of PXXPS (SEQ ID NO:1), SPXXP (SEQ ID NO:2), TLH (SEQ ID NO:3), QSXY (SEQ ID NO:4), LXSS (SEQ ID NO:21), PFXG (SEQ ID NO:22), or SIXA (SEQ ID NO:23), as expressed in an amino to carboxy orientation or in a carboxy to amino orientation.

In certain embodiments, the amino acid sequence that targets brain vascular endothelium comprises or consists of PYFPSLS (SEQ ID NO:5), YAPLTPS (SEQ ID NO:6), PLSPSAY (SEQ ID NO:7), DSPAHPS (SEQ ID NO:8), GTPTHPS (SEQ ID NO:9), PDAPSNH (SEQ ID NO:10), TEPHWPS (SEQ ID NO:11), SPPLPPK (SEQ ID NO:12), SPKPPPG (SEQ ID NO:13), NWSPWDP (SEQ ID NO:14), DSPAHPS (SEQ ID NO:15), GWTLHNK (SEQ ID NO:16), KIPPTLH (SEQ ID NO:17), ISQTLHG (SEQ ID NO:18), QSFYILT (SEQ ID NO:19), TTQSEYG (SEQ ID NO:20), MLVSSPA (SEQ ID NO:24), LPSSLQK (SEQ ID NO:25), PPLLKSS (SEQ ID NO:26), PXKLDSS (SEQ ID NO:27), AWTLASS (SEQ ID NO:28), WPFYGTP (SEQ ID NO:29), GTFPFLG (SEQ ID NO:30), GQVPFMG (SEQ ID NO:31), ANFSILA (SEQ ID NO:32), GSIWAPA (SEQ ID NO:33), or SIAASFS (SEQ ID NO:34), as expressed in an amino to carboxy orientation or in a carboxy to amino orientation.

In certain embodiments, the amino acid sequence that targets brain vascular endothelium comprises or consists of GMNAFRA (SEQ ID NO:41), as expressed in an amino to carboxy orientation or in a carboxy to amino orientation.

In certain embodiments, the amino acid sequence that targets brain vascular endothelium comprises at least one of SEQ ID NOs 1-4.

In certain embodiments, the amino acid sequence that targets brain vascular endothelium comprises at least one of SEQ ID NOs 21-23.

In certain embodiments, the amino acid sequence that targets brain vascular endothelium comprises at least one of SEQ ID NOs 5-20.

In certain embodiments, the amino acid sequence that targets brain vascular endothelium comprises at least one of SEQ ID NOs 24-34.

In certain embodiments, the amino acid sequence that targets brain vascular endothelium targets brain vascular endothelium in a subject that has a disease, e.g., a lysosomal storage disease.

In certain embodiments, the amino acid sequence that targets brain vascular endothelium targets brain vascular endothelium in a subject that does not have a lysosomal storage disease.

In certain embodiments, the viral vector comprises a nucleic acid sequence encoding a therapeutic agent. In certain embodiments, the therapeutic agent is β-glucuronidase.

In certain embodiments, the amino acid sequence that targets brain vascular endothelium is at most ten amino acids in length.

In certain embodiments, the amino acid sequence that targets brain vascular endothelium is 3, 4, 5, 6 or 7 amino acids in length.

Certain embodiments of the present disclosure provide a nucleic acid sequence encoding a viral vector as described herein.

Certain embodiments of the present disclosure provide a nucleic acid sequence encoding a modified capsid as described herein. Certain embodiments of the present disclosure provide a modified capsid encoded by a nucleic acid sequence described herein.

Certain embodiments of the present disclosure provide a cell comprising a viral vector as described herein.

Certain embodiments of the present disclosure provide a cell transduced by a viral vector as described herein.

In certain embodiments, the cell is a mammalian cell. In certain embodiments, the cell is a human cell. In certain embodiments, the cell is a non-human cell. In certain embodiments, the cell is in vitro. In certain embodiments, the cell is in vivo. In certain embodiments, the cell is an endothelial cell. In certain embodiments, the cell is a vascular endothelial cell.

Certain embodiments of the present disclosure provide a method of treating a disease in a mammal comprising administering a viral vector or the cell as described herein to the mammal.

In certain embodiments, the mammal is human.

In certain embodiments, the disease is a lysosomal storage disease (LSD).

In certain embodiments, the LSD is infantile or late infantile ceroid lipofuscinoses, Gaucher, Juvenile Batten, Fabry, MLD, Sanfilippo A, Late Infantile Batten, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease.

In certain embodiments, the disease is a neurodegenerative disease.

In certain embodiments, the neurodegenerative disease is Huntington's disease, ALS, hereditary spastic hemiplegia, primary lateral sclerosis, spinal muscular atrophy, Kennedy's disease, Alzheimer's disease, a polyglutamine repeat disease, or Parkinson's disease.

Certain embodiments of the present disclosure provide a method to deliver an agent to the central nervous system of a subject, comprising transducing vascular endothelial cells with a viral vector described herein so that the transduced vascular endothelial cells express the therapeutic agent and deliver the agent to the central nervous system of the subject.

In certain embodiments, the viral vector transduces vascular endothelial cells.

Certain embodiments of the present disclosure provide a viral vector or cell as described herein for use in medical treatment or diagnosis.

Certain embodiments of the present disclosure provide a use of a viral vector or cell as described herein to prepare a medicament useful for treating a disease, e.g., a lysosomal storage disease, in a mammal.

Certain embodiments of the present disclosure provide a method for identifying peptides that target brain vascular endothelium comprising using phage display biopanning so as to identify such peptides.

The vector may further comprise a lysosomal enzyme, a secreted protein, a nuclear protein, or a cytoplasmic protein. As used herein, the term "secreted protein" includes any secreted protein, whether naturally secreted or modified to contain a signal sequence so that it can be secreted. For example, the secreted protein could be β-glucuronidase, pepstatin insensitive protease, palmitoyl protein thioesterase.

Nucleic acid is "operably linked" when it is placed into a functional relationship with another nucleic acid sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

The vector may be an adeno-associated virus (AAV) vector, an adenoviral vector, a retrovirus, or a lentivirus vector based on human immunodeficiency virus or feline immunodeficiency virus. Examples of such AAVs are found in Davidson et al., PNAS (2000) 97:3428-3432. The AAV and lentiviruses can confer lasting expression while the adenovirus can provide transient expression.

The present disclosure also provides a mammalian cell containing a vector described herein. The cell may be human, and may be from brain, spleen, kidney, lung, heart, or liver. The cell type may be a stem or progenitor cell population.

The present disclosure provides a method of treating a disease such as a genetic disease or cancer in a mammal by administering a polynucleotide, polypeptide, expression vector, or cell described herein. The genetic disease or cancer may be a lysosomal storage disease (LSD) such as infantile or late infantile ceroid lipofuscinoses, Gaucher, Juvenile Batten, Fabry, MLD, Sanfilippo A, Late Infantile Batten, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease.

The genetic disease may be a neurodegenerative disease, such as Huntington's disease, ALS, hereditary spastic hemiplegia, primary lateral sclerosis, spinal muscular atrophy, Kennedy's disease, Alzheimer's disease, a polyglutamine repeat disease, or focal exposure such as Parkinson's disease.

Certain aspects of the disclosure relate to polynucleotides, polypeptides, vectors, and genetically engineered cells (modified in vivo), and the use of them. In particular, the disclosure relates to a method for gene or protein therapy that is capable of both systemic delivery of a therapeutically effective dose of the therapeutic agent.

According to one aspect, a cell expression system for expressing a therapeutic agent in a mammalian recipient is provided. The expression system (also referred to herein as a "genetically modified cell") comprises a cell and an expression vector for expressing the therapeutic agent. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector.

The expression vector further includes a promoter for controlling transcription of the heterologous gene. The promoter may be an inducible promoter (described below). The expression system is suitable for administration to the mammalian recipient. The expression system may comprise a plurality of non-immortalized genetically modified cells, each cell containing at least one recombinant gene encoding at least one therapeutic agent.

The cell expression system can be formed in vivo. According to yet another aspect, a method for treating a mammalian recipient in vivo is provided. The method includes introducing an expression vector for expressing a heterologous gene product into a cell of the patient in situ, such as via intravenous administration. To form the expression system in vivo, an expression vector for expressing the therapeutic agent is introduced in vivo into the mammalian recipient i.v., where the vector migrates via the vasculature to the brain.

According to yet another aspect, a method for treating a mammalian recipient in vivo is provided. The method includes introducing the target protein into the patient in vivo.

The expression vector for expressing the heterologous gene may include an inducible promoter for controlling transcription of the heterologous gene product. Accordingly, delivery of the therapeutic agent in situ is controlled by exposing the cell in situ to conditions, which induce transcription of the heterologous gene.

The mammalian recipient may have a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid or protein components.

According to one embodiment, the mammalian recipient has a genetic disease and the exogenous genetic material comprises a heterologous gene encoding a therapeutic agent for treating the disease. In yet another embodiment, the mammalian recipient has an acquired pathology and the exogenous genetic material comprises a heterologous gene encoding a therapeutic agent for treating the pathology. According to another embodiment, the patient has a cancer and the exogenous genetic material comprises a heterologous gene encoding an anti-neoplastic agent. In yet another embodiment the patient has an undesired medical condition and the exogenous genetic material comprises a heterologous gene encoding a therapeutic agent for treating the condition.

According to yet another embodiment, a pharmaceutical composition is disclosed. The pharmaceutical composition comprises a plurality of the above-described genetically modified cells or polypeptides and a pharmaceutically acceptable carrier. The pharmaceutical composition may be for treating a condition amenable to gene replacement therapy and the exogenous genetic material comprises a heterologous gene encoding a therapeutic agent for treating the condition. The pharmaceutical composition may contain an amount of genetically modified cells or polypeptides sufficient to deliver a therapeutically effective dose of the therapeutic agent to the patient. Exemplary conditions amenable to gene replacement therapy are described below.

According to another aspect, a method for forming the above-described pharmaceutical composition is provided. The method includes introducing an expression vector for expressing a heterologous gene product into a cell to form a genetically modified cell and placing the genetically modified cell in a pharmaceutically acceptable carrier.

These and other aspects, as well as various advantages and utilities will be more apparent with reference to the detailed description and to the accompanying Figures.

As used herein, the term "lysosomal enzyme," a "secreted protein," a "nuclear protein," or a "cytoplasmic protein" include variants or biologically active or inactive fragments of these polypeptides. A "variant" of one of the polypeptides is a polypeptide that is not completely identical to a native protein. Such variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The amino acid changes are achieved by changing the codons of the corresponding nucleic acid sequence. It is known that such polypeptides can be obtained based on substituting certain amino acids for other amino acids in the polypeptide structure in order to modify or improve biological activity. For example, through substitution of alternative amino acids, small conformational changes may be conferred upon a polypeptide that results in increased activity. Alternatively, amino acid substitutions in certain polypeptides may be used to provide residues, which may then be linked to other molecules to provide peptide-molecule conjugates which, retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a "protein", as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant protein has at least 50%, at least about 80%, or even at least about 90% but less than 100%, contiguous amino acid sequence homology or identity to the amino acid sequence of a corresponding native protein.

The amino acid sequence of the variant polypeptide corresponds essentially to the native polypeptide's amino acid sequence. As used herein "correspond essentially to" refers to a polypeptide sequence that will elicit a biological response substantially the same as the response generated by the native protein. Such a response may be at least 60% of the level generated by the native protein, and may even be at least 80% of the level generated by native protein.

A variant may include amino acid residues not present in the corresponding native protein or deletions relative to the corresponding native protein. A variant may also be a truncated "fragment" as compared to the corresponding native protein, i.e., only a portion of a full-length protein. Protein variants also include peptides having at least one D-amino acid.

The variant protein may be expressed from an isolated DNA sequence encoding the variant protein. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence. The terms "protein," "peptide" and "polypeptide" are used interchangeably herein.

The present disclosure provides methods of treating a disease in a mammal by administering an expression vector to a cell or patient. For the gene therapy methods, a person having ordinary skill in the art of molecular biology and gene therapy would be able to determine, without undue experimentation, the appropriate dosages and routes of administration of the expression vector used in the novel methods of the present disclosure.

According to one embodiment, the cells are transformed or otherwise genetically modified in vivo. The cells from the mammalian recipient are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into anti-sense RNA, as well as a "heterologous gene" (i.e., a gene encoding a protein which is not expressed or is expressed at biologically insignificant levels in a naturally-occurring cell of the same type).

In the certain embodiments, the mammalian recipient has a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid (e.g., antisense RNA) and/or protein components.

A number of lysosomal storage diseases are known (for example Neimann-Pick disease, Sly syndrome, Gaucher Disease). Other examples of lysosomal storage diseases are provided in Table 1. Therapeutic agents effective against these diseases are also known, since it is the protein/enzyme known to be deficient in these disorders.

TABLE 1

List of putative target diseases for gene therapies.
Disease

Gaucher
Juvenile Batten
Fabry
MLD
Sanfilippo A
Late Infantile Batten
Hunter
Krabbe
Morquio
Pompe
Niemann-Pick C
Tay-Sachs
Hurler (MPS-I H)
Sanfilippo B
Maroteaux-Lamy
Niemann-Pick A
Cystinosis
Hurler-Scheie (MPS-I H/S)
Sly Syndrome (MPS VII)
Scheie (MPS-I S)
Infantile Batten
GM1 Gangliosidosis
Mucolipidosis type II/III
Sandhoff
other As used herein, "acquired pathology" refers to a disease or syndrome manifested by an abnormal physiological, biochemical, cellular, structural, or molecular biological state. Exemplary acquired pathologies, are provided in Table 2. Therapeutic agents effective against these diseases are also given.

TABLE II

Potential Gene Therapies for Motor Neuron Diseases and other neurodegenerative diseases.

| Disease | Candidates for Gene Replacement[2] | Candidates for Downstream Effectors[3] | Neuronal or Progenitor Cell Replacement[4] |
|---|---|---|---|
| ALS | No | Yes | Yes |
| Hereditary spastic hemiplegia | Spastin, paraplegin | Yes | Yes |
| Primary lateral sclerosis[5] | No | Yes | Yes |
| Spinal muscular atrophy | Survival motor neuron gene, neuronal apoptosis inhibiting factor | Yes | Yes |
| Kennedy's disease | Androgen-receptor element | Yes | Yes |
| Alzheimer's disease | | Yes | Yes |
| Polyglutamine Repeat Diseases | | Yes | Yes |

[2]Based on current literature.
[3]Based on current literature, includes calbindin, trophic factors, bcl-2, neurofilaments, and pharmacologic agents.
[4]May include cell- or cell- and gene-based therapies.
[5]A sporadic degeneration of corticospinal neurons, 1/100th as common as ALS, with no known genetic links.

Alternatively, the condition amenable to gene replacement therapy is a prophylactic process, i.e., a process for preventing disease or an undesired medical condition. Thus, the instant disclosure embraces a cell expression system for delivering a therapeutic agent that has a prophylactic function (i.e., a prophylactic agent) to the mammalian recipient.

In summary, the term "therapeutic agent" includes, but is not limited to, the agents listed in the Tables above, as well as their functional equivalents. As used herein, the term "functional equivalent" refers to a molecule (e.g., a peptide or protein) that has the same or an improved beneficial effect on the mammalian recipient as the therapeutic agent of which is it deemed a functional equivalent. As will be appreciated by one of ordinary skill in the art, a functionally equivalent proteins can be produced by recombinant techniques, e.g., by expressing a "functionally equivalent DNA." As used herein, the term "functionally equivalent DNA" refers to a non-naturally occurring DNA, which encodes a therapeutic agent. For example, many, if not all, of the agents disclosed in Tables 1-2 have known amino acid sequences, which are encoded by naturally occurring nucleic acids. However, due to the degeneracy of the genetic code, more than one nucleic acid can encode the same therapeutic agent. Accordingly, the instant disclosure embraces therapeutic agents encoded by naturally-occurring DNAs, as well as by non-naturally-occurring DNAs, which encode the same protein as, encoded by the naturally-occurring DNA.

The above-disclosed therapeutic agents and conditions amenable to gene replacement therapy are merely illustrative and are not intended to limit the scope of the instant disclosure. The selection of a suitable therapeutic agent for treating a known condition is deemed to be within the scope of one of ordinary skill of the art without undue experimentation.

Screening Methods

The present disclosure provides methods to screen for and identify amino acid sequences that target, e.g., specifically target, a specific area, such as the vasculature of the central nervous system. This method can be used to identify targeting sequences that are specific for specific disease states. In other words, targeting sequences may be identified and used in the treatment of specific diseases.

AAV Vectors

Adeno associated virus (AAV) is a small (20 nm), non-pathogenic virus that is useful in treating human brain diseases, such as Parkinson's disease and recessive genetic diseases. A construct is generated that surrounds a promoter linked to a beta-glucuronidase gene with AAV ITR sequences.

In one embodiment, a viral vector of the disclosure is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-8. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped rAAV are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See for example Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.). As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from any of several AAV serotypes, including without limitation, AAV-1, AAV-2, AAV-3, AAV-4, AAV-5, AAV6, or AAV8, and the AAV ITRS are derived form AAV serotype 2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In some embodiments of the disclosure the DNA molecules for use in the AAV vectors will contain one or more copies of a single siRNA sequence. As used herein the term multiple copies of an siRNA sequences means at least 2 copies, at least 3 copies, at least 4 copies, at least 5 copies, at least 6 copies, at least 7 copies, at least 8 copies, at least 9 copies, and at least 10 copies. In some embodiments the DNA molecules for use in the AAV vectors will contain multiple siRNA sequences. As used herein the term multiple siRNA sequences means at least 2 siRNA sequences, at least 3 siRNA sequences, at least 4 siRNA sequences, at least 5 siRNA sequences, at least 6 siRNA sequences, at least 7 siRNA sequences, at least 8 siRNA sequences, at least 9 siRNA sequences, and at least 10 siRNA sequences. In some embodiments suitable DNA vectors of the disclosure will contain a sequence encoding the siRNA molecule of the disclosure and a stuffer fragment. Suitable stuffer fragments of the disclosure include sequences known in the art including without limitation sequences which do not encode an expressed protein molecule; sequences which encode a normal cellular protein which would not have deleterious effect on the cell types in which it was expressed; and sequences which would not themselves encode a functional siRNA duplex molecule.

In one embodiment, suitable DNA molecules for use in AAV vectors will be less than about 5 kilobases (kb) in size and will include, for example, a stuffer sequence and a sequence encoding a siRNA molecule of the disclosure. For example, in order to prevent any packaging of AAV genomic sequences containing the rep and cap genes, a plasmid containing the rep and cap DNA fragment may be modified by the inclusion of a stuffer fragment as is known in the art into the AAV genome which causes the DNA to exceed the length for optimal packaging. Thus, the helper fragment is not packaged into AAV virions. This is a safety feature, ensuring that only a recombinant AAV vector genome that does not exceed optimal packaging size is packaged into virions. An AAV helper fragment that incorporates a stuffer sequence can exceed the wild-type genome length of 4.6 kb, and lengths above 105% of the wild-type will generally not be packaged.

The stuffer fragment can be derived from, for example, such non-viral sources as the Lac-Z or beta-galactosidase gene.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In one embodiment, both heterologous promoters and other control elements, such as CNS-specific and inducible promoters, enhancers and the like, will be of particular use. Examples of heterologous promoters include the CMB promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM $MgCl_2$, 10 mM DTT, 33 µg/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct micro-injection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

In one embodiment, host cells containing the above-described AAV expression vectors are rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors have been described which encode Rep and/or Cap expression products.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors have been described which encode Rep and/or Cap expression products.

In one embodiment, both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the disclosure include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

In one embodiment, the host cell (or packaging cell) is rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In one embodiment, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents.

In one embodiment, accessory functions are provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a host cell to provide accessory functions.

In one embodiment, nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. Specifically, early adenoviral gene regions E1a, E2a, E4, VAI RNA and, possibly, E1b are thought to participate in the accessory process. Herpesvirus-derived accessory functions have been described. Vaccinia virus-derived accessory functions have also been described.

In one embodiment, as a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

In one embodiment, following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile. The resulting rAAV virions are then ready for use for DNA delivery to the CNS (e.g., cranial cavity) of the subject.

Methods of delivery of viral vectors include, but are not limited to, intra-arterial, intra-muscular, intravenous, intranasal and oral routes. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, for in vivo delivery, the rAAV virions are formulated into pharmaceutical compositions and will generally be administered parenterally, e.g., by intramuscular injection directly into skeletal or cardiac muscle or by injection into the CNS.

In one embodiment, viral vectors are delivered to the CNS via convection-enhanced delivery (CED) systems that can efficiently deliver viral vectors, e.g., AAV, over large regions of a subject's brain (e.g., striatum and/or cortex). As described in detail and exemplified below, these methods are suitable for a variety of viral vectors, for instance AAV vectors carrying therapeutic genes (e.g., siRNAs).

Any convection-enhanced delivery device may be appropriate for delivery of viral vectors. In one embodiment, the device is an osmotic pump or an infusion pump. Both osmotic and infusion pumps are commercially available from a variety of suppliers, for example Alzet Corporation, Hamilton Corporation, Aiza, Inc., Palo Alto, Calif.). Typically, a viral vector is delivered via CED devices as follows. A catheter, cannula or other injection device is inserted into CNS tissue in the chosen subject. In view of the teachings herein, one of skill in the art could readily determine which general area of the CNS is an appropriate target. For example, when delivering AAV vector encoding a therapeutic gene to treat PD, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the viral vectors, fewer infusion cannula are needed. Since surgical complications are related to the number of penetrations, the methods described herein also serve to reduce the side effects seen with conventional delivery techniques.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present disclosure be combined with other suitable compositions and therapies.

Methods for Introducing Genetic Material into Cells

The exogenous genetic material (e.g., a cDNA encoding one or more therapeutic proteins) is introduced into the cell ex vivo or in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-faciliated microparticle bombardment. Strontium phosphate DNA co-precipitation is another possible transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any non-translated DNA sequence which works contiguous with the coding sequence (in cis) to change the basal transcription level dictated by the promoter. The exogenous genetic material may introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eucaryotic cells. These include: the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The therapeutic agent can be targeted for delivery to an extracellular, intracellular or membrane location. If it is desirable for the gene product to be secreted from the cells, the expression vector is designed to include an appropriate secretion "signal" sequence for secreting the therapeutic gene product from the cell to the extracellular milieu. If it is desirable for the gene product to be retained within the cell, this secretion signal sequence is omitted. In a similar manner, the expression vector can be constructed to include "retention" signal sequences for anchoring the therapeutic agent within the cell plasma membrane. For example, all membrane proteins have hydrophobic transmembrane regions, which stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

The following discussion is directed to various utilities of the instant disclosure. For example, the instant disclosure has utility as an expression system suitable for detoxifying intra- and/or extracellular toxins in situ. By attaching or omitting the appropriate signal sequence to a gene encoding a therapeutic agent capable of detoxifying a toxin, the therapeutic agent can be targeted for delivery to the extracellular milieu, to the cell plasma membrane or to an intracellular location. In one embodiment, the exogenous genetic material containing a gene encoding an intracellular detoxifying therapeutic agent, further includes sequences encoding surface receptors for facilitating transport of extracellular toxins into the cell where they can be detoxified intracellularly by the therapeutic agent. Alternatively, the cells can be genetically modified to express the detoxifying therapeutic agent anchored within the cell plasma membrane such that the active portion extends into the extracellular milieu. The active portion of the membrane-bound therapeutic agent detoxifies toxins, which are present in the extracellular milieu.

In addition to the above-described therapeutic agents, some of which are targeted for intracellular retention, the instant disclosure also embraces agents intended for delivery to the extracellular milieu and/or agents intended to be anchored in the cell plasma membrane.

The selection and optimization of a particular expression vector for expressing a specific gene product in an isolated cell is accomplished by obtaining the gene, potentially with one or more appropriate control regions (e.g., promoter, insertion sequence); preparing a vector construct comprising the vector into which is inserted the gene; transfecting or transducing cultured cells in vitro with the vector construct; and determining whether the gene product is present in the cultured cells.

In certain embodiments, a virus from the adeno-associated virus family is used. In certain embodiments, an expression vector for gene therapy based on AAV2, AAV4 and/or AAV5 is used.

Thus, as will be apparent to one of ordinary skill in the art, a variety of suitable viral expression vectors are available for transferring exogenous genetic material into cells. The selection of an appropriate expression vector to express a therapeutic agent for a particular condition amenable to gene replacement therapy and the optimization of the conditions for insertion of the selected expression vector into the cell, are within the scope of one of ordinary skill in the art without the need for undue experimentation.

In an alternative embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

The instant disclosure also provides various methods for making and using the above-described genetically-modified cells. As used herein, the term "isolated" means a cell or a plurality of cells that have been removed from their naturally-occurring in vivo location. Methods for removing cells from a patient, as well as methods for maintaining the isolated cells in culture are known to those of ordinary skill in the art.

The instant disclosure also provides methods for genetically modifying cells of a mammalian recipient in vivo. According to one embodiment, the method comprises introducing an expression vector for expressing a heterologous gene product into cells of the mammalian recipient in situ by, for example, injecting the vector into the recipient.

In one embodiment, the preparation of genetically modified cells contains an amount of cells sufficient to deliver a therapeutically effective dose of the therapeutic agent to the recipient in situ. The determination of a therapeutically effective dose of a specific therapeutic agent for a known condition is within the scope of one of ordinary skill in the art without the need for undue experimentation. Thus, in determining the effective dose, one of ordinary skill would consider the condition of the patient, the severity of the condition, as well as the results of clinical studies of the specific therapeutic agent being administered.

If the genetically modified cells are not already present in a pharmaceutically acceptable carrier they are placed in such a carrier prior to administration to the recipient. Such pharmaceutically acceptable carriers include, for example, isotonic saline and other buffers as appropriate to the patient and therapy.

More than one recombinant gene can be introduced into each genetically modified cell on the same or different vectors, thereby allowing the expression of multiple therapeutic agents by a single cell.

EXAMPLE 1

Treating Central Nervous System Disorders by Means of Vascular Endothelia

Lysosomal storage disorders (LSDs) constitute a large class of inherited metabolic disorders. Most LSDs are caused by lysosomal enzyme deficiencies which lead to organ damage and often central nervous system (CNS) degeneration. Early work in rodent models of the lysosomal storage diseases (LSD) has shown promise in addressing the systemic manifestations of these disorders, either by enzyme replacement or bone marrow transplant to adult recipients. While enzyme replacement is efficacious for peripheral disease, treating the CNS remains a challenge as enzymes delivered intravenously do not cross the blood-brain barrier (BBB). Gene therapy studies in LSD animal models have thus far required direct intracranial injection of viral vectors. The cerebral vasculature is an attractive target for gene therapy due to its extensive network throughout the brain that may potentially be co-opted to deliver therapeutic enzymes, but a vector that targets the vasculature is not available. Here the inventors used in vivo phage display to identify peptides that bind to the vascular endothelia of a murine model of mucopolysaccharidosis type VII (MPS VII), a prototypical LSD caused by β-glucuronidase deficiency. In the β-glucuronidase deficient mouse, inhibition of cognitive decline required that treatment be initiated in the neonatal period systemically prior to blood-brain barrier closure, or directly to brain. Insertion of the newly identified peptides into the adeno-associated virus capsid resulted in virus that expressed therapeutic enzyme from vascular endothelial cells. Importantly, intravenous injection of the modified virus rescued CNS deficits in the MPS VII mouse. These results demonstrate for the first time therapeutic efficacy based on retargeting viral tropism to a critical site of disease.

Figure 1B:
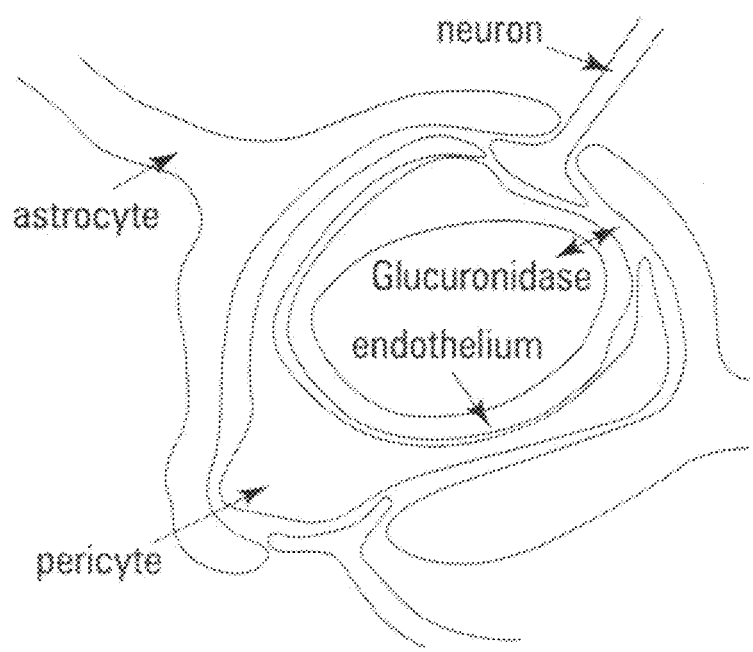

Prior studies have shown that soluble lysosomal enzymes are in part secreted out of the cell, and can undergo mannose-6-phosphate receptor mediated endocytosis and sorting to the lysosome by neighboring cells in a process termed cross correction. The inventors hypothesized that expression of lysosomal enzymes from brain vascular endothelia would lead to global cross correction of the brain by virtue of the dense distribution of CNS vasculature throughout the brain parenchyma. The surface area of the brain microvasculature is about 100 $cm^2$/g of tissue. Transduction of vascular endothelial cells allows apical and basolateral secretion of therapeutic agents such as β-glucuronidase. Thus, the inventors hypothesized that basolateral secretion can expose underlying neurons and glia to recombinant enzyme sufficient for therapy (FIGS. 1A and 1B). Currently, no AAVs target brain endothelium specifically or efficiently. Most AAVs are taken up by liver following peripheral delivery.

The present inventors designed AAVs that are modified to target brain endothelia after systemic delivery. To generate an adeno-associated virus (AAV) that targets the cerebral vasculature, the inventors first used in vivo phage display panning to identify peptide motifs that bind preferentially to brain vasculature. A phage-display library was injected intravenously into wildtype and MPS VII mice, and the brain microvasculature was subsequently isolated along with the bound phage. The isolated phage was then amplified and reinjected, and after five rounds of such in vivo panning, DNA sequencing of the recovered phage revealed an enrichment of distinct peptide motifs from the initial phage library. Interestingly, the motifs enriched in wildtype mice were all distinct from those in MPSVII mice, suggesting a vascular remodeling process in the diseased mice. This method can be utilized to identify motif(s) that are specific to other disease states.

Figure 2C:
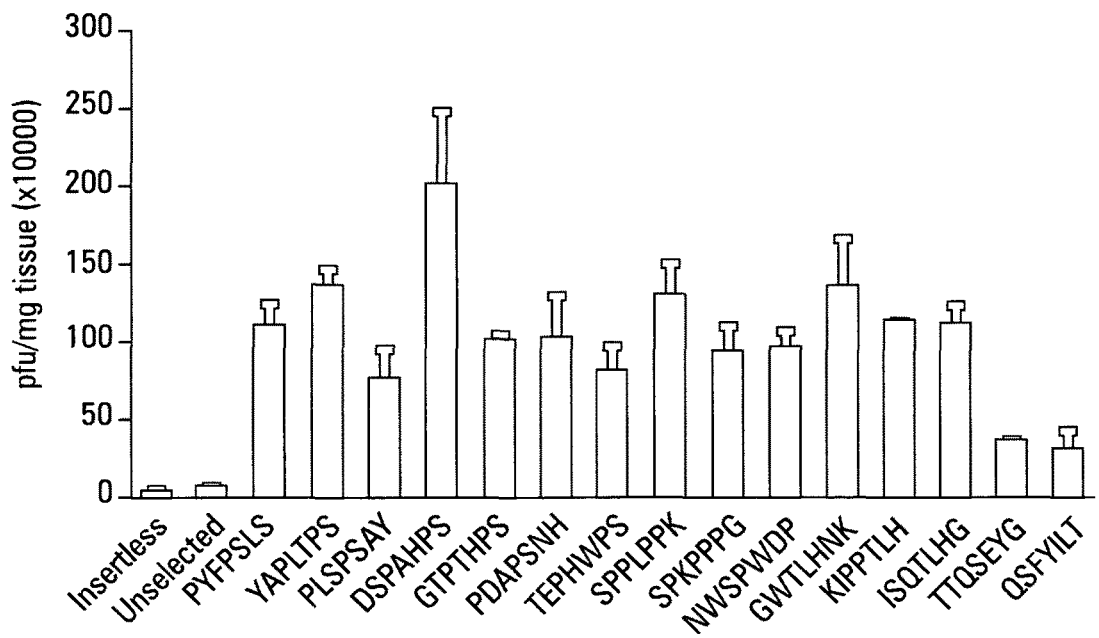
Figure 2D:
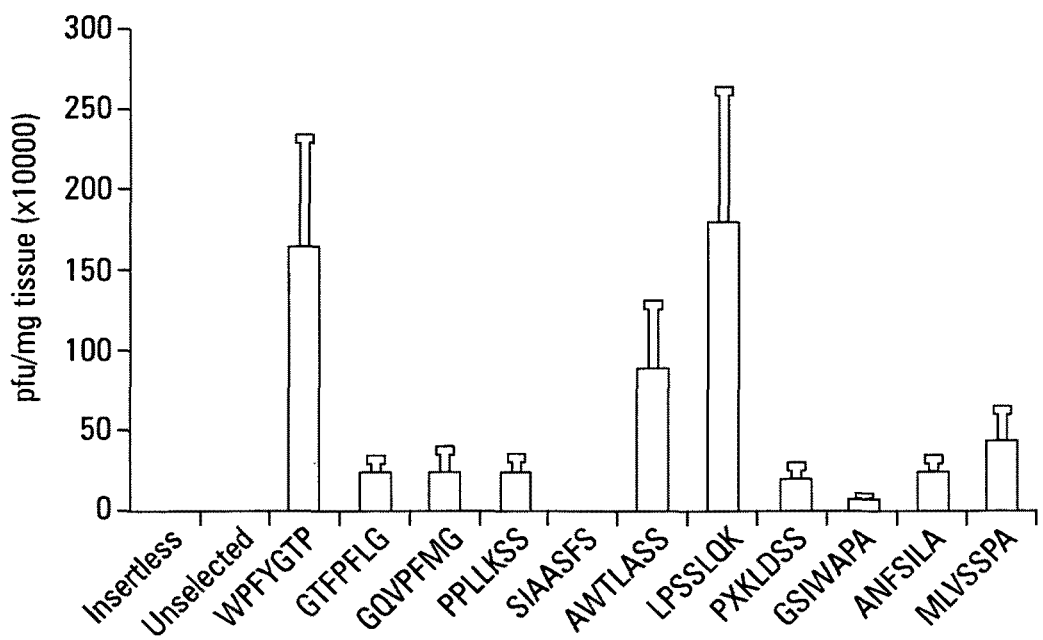

In wildtype mice, the peptide motifs, PxxPS (SEQ ID NO: 1), SPxxP (SEQ ID NO: 2). TLH (SEQ ID NO: 3) and QSxY (SEQ ID NO: 4) were identified in 19 of the clones (FIG. 2A). Of these, two peptides were especially notable, namely DSPAHPS (SEQ ID NO: 8) and GWTLHNK (SEQ ID NO: 16). DSPAHPS (SEQ ID NO: 15) contained both PxxPS (SEQ ID NO: 1) and SPxxP (SEQ ID NO: 2) motifs, and GWTLHNK (SEQ ID NO: 16) was represented 3 times in the sampled phage population. In MPS VII mice, three peptides motifs—LxSS (SEQ ID NO: 21), PFxG (SEQ ID NO: 22) and SIxA (SEQ ID NO: 23)—were identified (FIG. 2B). To confirm the affinity of these phage for the brain vasculature, each phage was individually re-injected intravenously into wildtype or MPS VII mice, and the amount of phage recovered from brain vasculature was compared to that of either a control phage without a peptide insert, or the original unselected phage library. In wildtype mice, the recovery of phage containing DSPAHPS (SEQ ID NO: 8) and GWTLHNK (SEQ ID NO: 16) was higher than the others (FIG. 2C), consistent with the initial panning results. In MPS VII mice, the peptides WPFYGTP (SEQ ID NO: 29) and LPSSLQK (SEQ ID NO: 25) were more highly-recovered than the other selected phage (FIG. 2D). Consistent with the panning results, each of the selected phage accumulated in brain beyond the background levels observed for controls.

Peptide-modified AAVs were generated by inserting the peptides identified from phage display panning into the AAV2 capsid. Peptides were inserted at position 587 of the VP3 capsid protein to yield clones AAV-Linker(AAAAA (SEQ ID NO: 44)), AAV-TLH(GWTLHNK (SEQ ID NO: 16)), AAV-PPS(DSPAHPS (SEQ ID NO: 8)), AAV-PFG(WPFYGTP (SEQ ID NO: 29)) and AAV-LSS(LPSSLQK (SEQ ID NO: 25)). AAV-WT (no insert) served as a control virus. The 587 site is located in a domain of the VP3 capsid protein involved in the binding of AAV2 with its major receptor, heparin sulfate proteoglycan (HSPG), and insertion of peptides in this site can alter the tropism of AAV without compromising virus viability. The modified capsid proteins packaged AAV vector genomes with genomic titers comparable to those of wildtype virus.

To assess the tissue tropism of the peptide-modified AAV, the investigators quantified viral genomes by RT-PCR in liver and brain following tail vein injections of virus. AAV-PPS and AAV-TLH were injected into wildtype mice, and AAV-PFG and AAV-LSS were injected into MPS VII mice. A design for peptide modified AAVs (PM-AAVs) is depicted in Scheme 1 below.

SCHEME 1

1. Sequence of AAV2 wild-type capsid

```
          587 588
5'-AGA GGC AAC AGA CAA GCA-3'              (SEQ ID NO: 36)
   R   G   N   R   Q   A                   (SEQ ID NO: 37)
```

2. Modified sequence of capsid backbone

```
              Not I           AscI
5'-AGA GGC AAC GCG GCC GCC TAG GCG CGC CAA GCA-3' (SEQ ID NO: 38)
   R   G   N   A   A   A  stop A   R   Q   A     (SEQ ID NO: 39)
```

3. Insertion of peptide X into the NotI and AscI site

```
   R   G   N   A   A   A   X   A   A   R   Q   N  (SEQ ID NO: 40)
```

The sequence of AAV2 wild type capsid is depicted below in SEQ ID NO:35. An example of amino acids targeted to brain vasculature of MPS VII mice are italicized, and the underlined amino acids are spacers.

(SEQ ID NO: 35)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

-continued
QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGN*AAAWPFYGTPAA*R

QAATADVNTQGVLPGMVWQDRDVYLQGPIWAKIPHTDGHFHPSPLMGGFG

LKHPPPQILIKNTPVPANPSTTFSAAKFASFITQYSTGQVSVEIEWELQK

ENSKRWNPEIQYTSNYNKSVNVDFTVDTNGVYSEPRPIGTRYLTRNL*

Figure 3A:
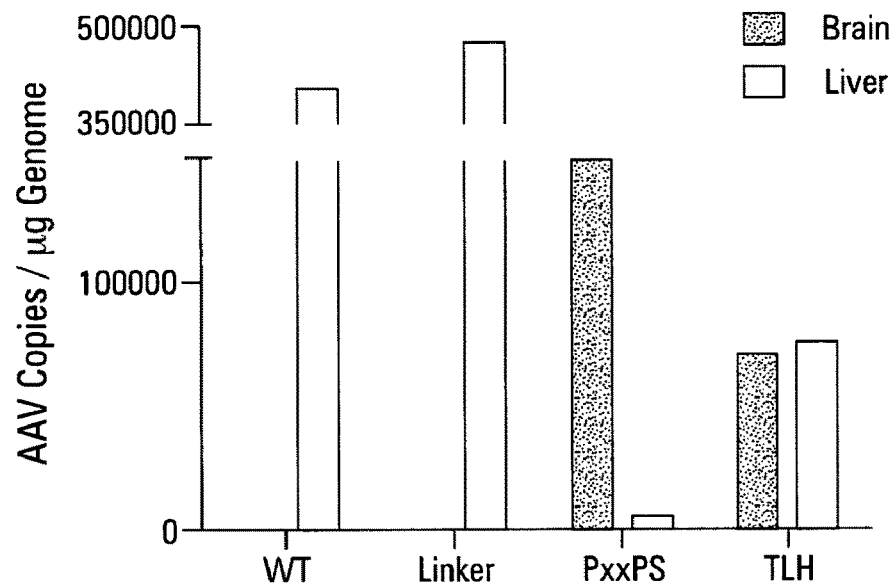
FIGS. 3A-3B. Peptide-modified virus exhibits selective transduction of cerebral vasculature independent of heparin sulfate.
Figure 3B:
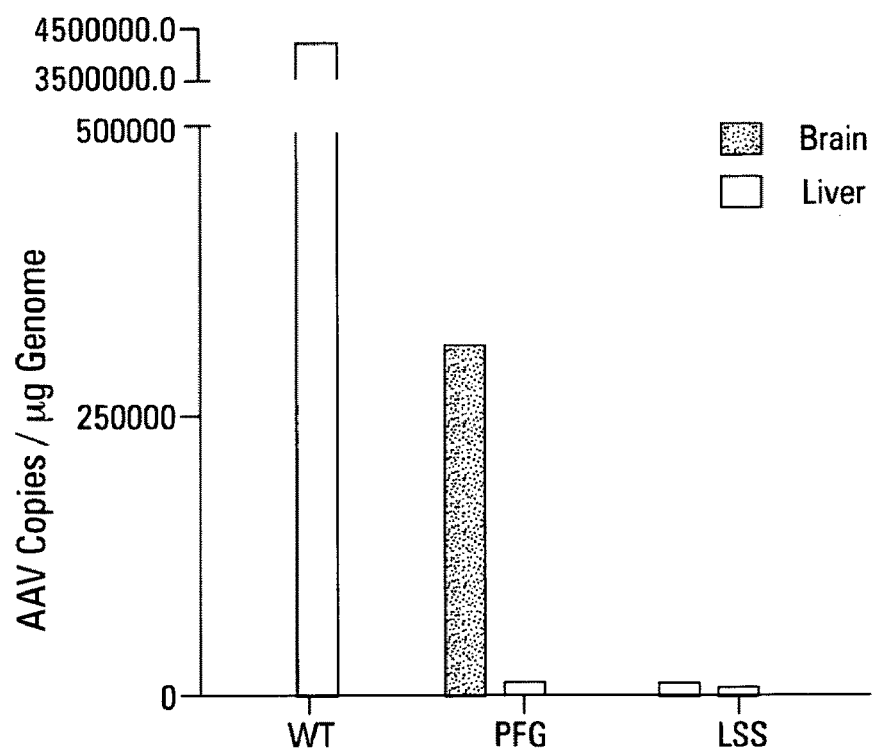

AAV-WT was injected as a control in both mouse strains. At four weeks post-injection, AAV-WT transduced the liver predominantly, with no virus detected in the brain of either wildtype or MPS VII mice after systemic administration (FIGS. 3A and 3B). In contrast, intravenous administration of peptide-modified AAV resulted in significant virus accumulation in the brain and lower levels in the liver (FIGS. 3A and 3B). The tropism of peptide-modified AAV was further confirmed by reporter gene expression. Peptide-modified AAV with the cytomegalovirus (CMV) promoter driving expression of either eGFP (AAV-PPS) or β-glucuronidase (AAV-PFG) was injected via tail vein in wildtype and MPS VII mice, respectively. Consistent with the RT-PCR results, at 4 weeks post-injection, eGFP and β-glucuronidase expression was detected in the brain of wildtype and MPS VII mice, respectively, and not observed in mice infused with AAV-WT. Furthermore, β-glucuronidase co-localized with CD31, a marker of vascular endothelium, confirming that the virus is targeting brain endothelium. The shift in tropism of these modified AAV is accompanied by a loss in affinity to heparin sulfate proteoglycan. In a heparin-agarose binding assay, AAV-TLH, AAV-PPS, AAV-PFG and AAV-LSS all lost the ability to bind heparin sulfate. These results demonstrate that the peptides currently identified via phage display panning successfully retargeted the tropism of AAV to the brain vascular endothelium.

Thus, in certain embodiments, an amino acid sequence that targets the vector to brain vascular endothelium is inserted, as discussed above. In certain embodiments, that amino acid sequence may consist of, or comprise, PXXPS (SEQ ID NO:1), SPXXP (SEQ ID NO:2), TLH (SEQ ID NO:3), QSXY (SEQ ID NO:4), LXSS (SEQ ID NO:21), PFXG (SEQ ID NO:22), or SIXA (SEQ ID NO:23), as expressed in an amino to carboxy orientation or in a carboxy to amino orientation. In certain embodiments, that sequence may consist of, or comprise, PYFPSLS (SEQ ID NO:5), YAPLTPS (SEQ ID NO:6), PLSPSAY (SEQ ID NO:7), DSPAHPS (SEQ ID NO:8), GTPTHPS (SEQ ID NO:9), PDAPSNH (SEQ ID NO:10), TEPHWPS (SEQ ID NO:11), SPPLPPK (SEQ ID NO:12), SPKPPPG (SEQ ID NO:13), NWSPWDP (SEQ ID NO:14), DSPAHPS (SEQ ID NO:15), GWTLHNK (SEQ ID NO:16), KIPPTLH (SEQ ID NO:17), ISQTLHG (SEQ ID NO:18), QSFYILT (SEQ ID NO:19), TTQSEYG (SEQ ID NO:20), MLVSSPA (SEQ ID NO:24), LPSSLQK (SEQ ID NO:25), PPLLKSS (SEQ ID NO:26), PXKLDSS (SEQ ID NO:27), AWTLASS (SEQ ID NO:28), WPFYGTP (SEQ ID NO:29), GTFPFLG (SEQ ID NO:30), GQVPFMG (SEQ ID NO:31), ANFSILA (SEQ ID NO:32), GSIWAPA (SEQ ID NO:33), or SIAASFS (SEQ ID NO:34), as expressed in an amino to carboxy orientation or in a carboxy to amino orientation.

Delivery of therapeutic enzymes to the central nervous system continues to be a major challenge in treating neuronopathic lysosomal storage disorders as the blood brain barrier effectively prevents entry of enzymes from the systemic circulation. Here the investigators tested the therapeutic efficacy of targeting brain vascular endothelia with the modified AAV in the murine model of MPS VII. This β-glucuronidase-deficient mouse exhibits hallmarks of MPS VII disease including lysosomal storage, and neurological dysfunction, and is a proven model for investigating novel therapies for lysosomal storage disorders (Vogler, C. et al., *Pediatr Res* 49, 342-8 (2001)). AAV-PFG or AAV-WT expressing β-glucuronidase was injected via tail vein in the MPS VII mice at 6 weeks of age, a time when lysosomal storage deposits first appear in the mouse. At 6 weeks post-injection, lysosomal storage and cellular distension in the brain was investigated via brightfield microscopy. MPS VII mice treated with AAV-PFG exhibited reduced levels of lysosomal storage relative to mice receiving AAV-WT, which retained lysosomal storage in multiple regions of the CNS, including cerebral cortex, hippocampus, striatum, and cerebellum (FIGS. 4A-4H). Because the present peptide-modified viruses specifically target endothelia, the correction of neuronal pathology suggests that β-glucuronidase is secreted basolaterally by endothelial cells and subsequently cross-correcting adjacent neurons. The correction of neuropathology in multiple structures throughout the entire rostral-caudal extent of the brain indicates a broad dissemination of therapeutic enzyme.

Figure 4A:
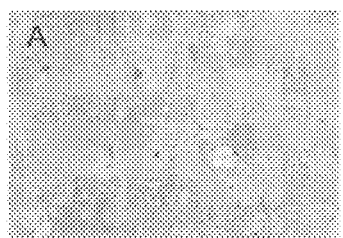
FIGS. 4A-4K. Intravenous delivery of peptide-modified virus rescues neuropathology and CNS deficits of MPS VII mice.
Figure 4B:
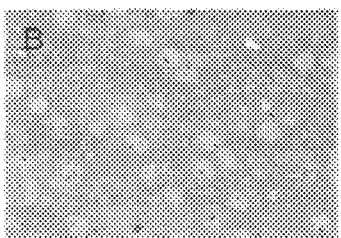
Figure 4C:
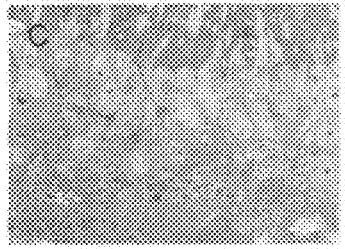
Figure 4D:
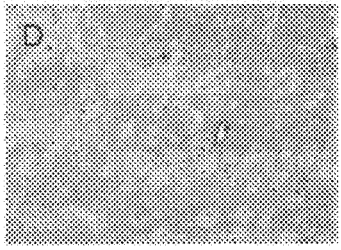
Figure 4E:
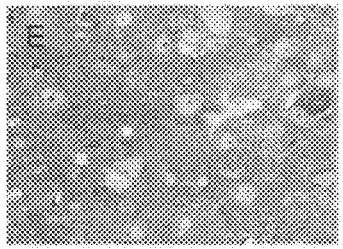
Figure 4F:
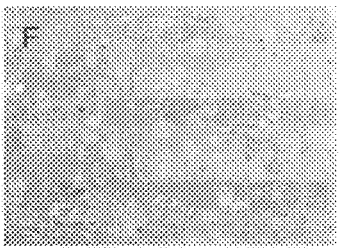
Figure 4G:
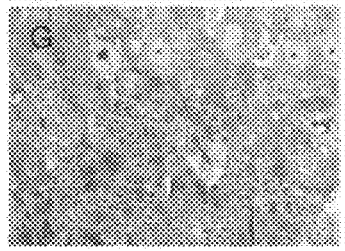
Figure 4H:
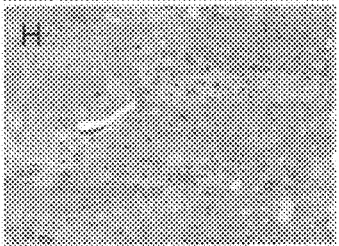
Figure 4I:
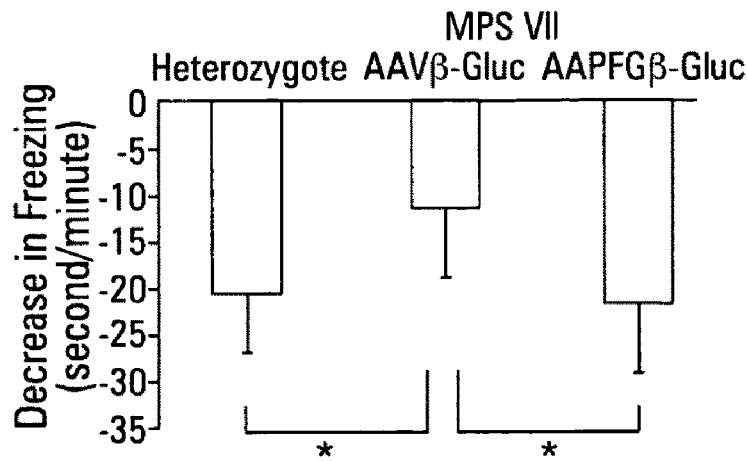

MPS VII mice develop progressive impairment of neuronal function as measured by Morris water maze, repeated acquisition and performance chamber (RAPC), and context fear-conditioning assays. To test for functional recovery after intravenous delivery of PM-AAV, the present investigators used the context fear-conditioning assay, which tests the integrity of several brain regions including the hippocampus and the amygdala. Mice were first conditioned by foot-shocks in the testing chamber (context 1). One day later, fear-induced freezing behavior was measured when the mice were placed either in context 1 or a modified chamber with novel olfactory, tactile, and visual cues (context 2). Control mice were able to distinguish context 1 from context 2, as evidenced by the decrease in freezing behavior when placed in context 2. MPS VII mice treated with AAV-WT-β-glucuronidase, in contrast, exhibited less change in freezing behavior, suggesting the persistence of memory deficits. MPS VII mice treated with AAV-PFG-β-glucuronidase, however, exhibited behavior similar to that of heterozygous mice (FIG. 4I). Intravenous injection of PM-AAV, and subsequent expression of β-glucuronidase from brain endothelia, rescued these CNS deficits of the MPS VII mouse.

Figure 4J:
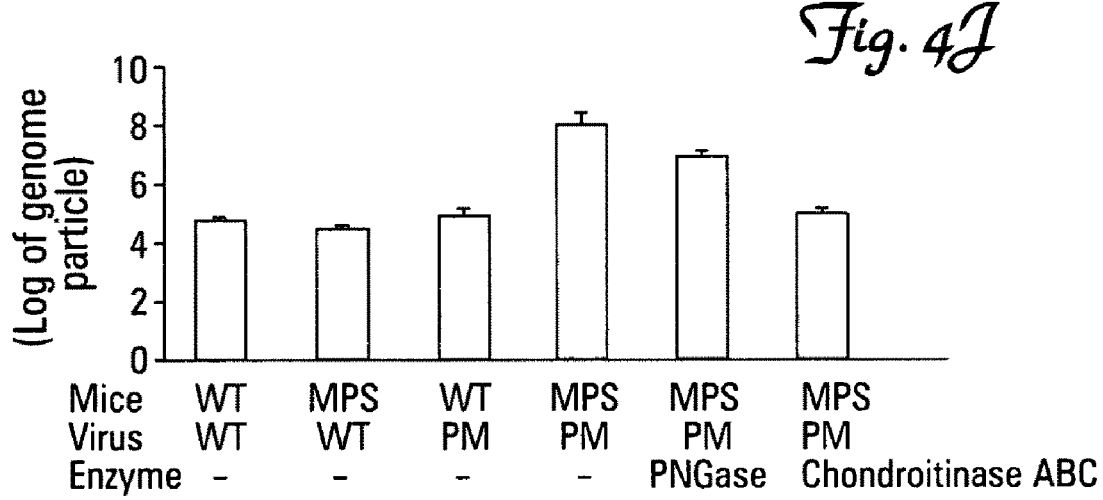
Figure 4K:
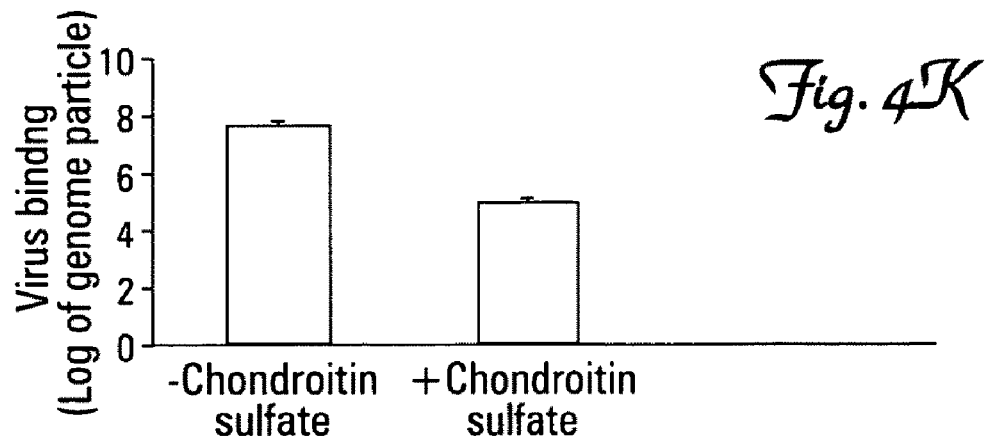

The deficient enzyme in MPS VII, β-glucuronidase, catalyzes the degradation of glycosaminoglycans (GAG's) including heparin sulfate and chondroitin sulfate. In the disease state, catabolism of these molecules is blocked and results in lysosomal accumulation. The investigators hypothesized that peptide-modified AAV might interact with GAG-containing glycoproteins that accumulate on endothelial surfaces. To address this hypothesis, the ability of AAV-PFG to bind to purified brain vasculature from MPS VII mice in the presence and absence of the enzyme chondroitinase ABC was measured. Enzymatic treatment of the vasculature from MPS VII mice abolished the binding ability to the PFG-AAV (FIG. 4J). It was further demonstrated that an excess of chondroitin sulfate in the binding reaction was able to compete away the binding of PFG-AAV to the vasculature (FIG. 4K). These results suggest that the binding of the present modified virus (AAV-PFG) to the brain vascular endothelia requires chondroitin sulfate.

As proof of principle that the success of the panning experiments is applicable to disease models beyond the MPS VII mouse, the present investigators carried out the same experiment in a mouse model of late infantile neuronal ceroid lipofuscinosis. This mouse lacks expression of the lysosomal enzyme tripeptidyl peptidase I (TPP1), and recapitulates many pathological features of the human disease. After five rounds of in vivo panning, a single dominant peptide emerged-GMNAFRA (SEQ ID NO:41) (FIG. 5A). As before, a peptide-modified AAV expressing TPP1 was produced and injected intravenously in TPP1-deficient mice. Three weeks post-injection, mice that received PM-AAV exhibited TPP1 expression in small vessels of the cerebral cortex, midbrain, and cerebellum, whereas mice that received injections of wildtype AAV did not show any TPP1 staining (FIGS. 5B-5D). The peptide identified in this experiment was distinct from those in wildtype or MPS VII mice, again suggesting a disease-specific vascular remodeling process. An in vitro assay for TPP1 activity in several tissues following tail vein injection of peptide modified virus was also performed (FIG. 5E). Activity levels expressed relative to heterozygous control.

The ability to systematically alter viral tropism has emerged as a powerful technique for gene therapy. Here the present investigators retargeted AAV to the brain vasculature as a means to disseminate therapeutic enzyme, and demonstrated for the first time a correction of CNS disease in the MPS VII mouse following peripheral delivery of gene therapy vectors.

Thus, peripheral delivery of peptide-modified AAVs targeted to the brain treated pathology and improved behavioral deficits when delivered to adult mice with established disease. Modified vectors, e.g., peptide-modified AAVs, can be used in therapies for the CNS aspects of the LSDs.

The inventors also studied the in vivo biodistribution of peptide modified AAV. Peptide-modified AAV ($1.0 \times 10^{11}$ GPs) were injected intravenously into mice, with AAV-PPS and AAV-TLH to wild type mice, AAV-PFG and AAV-LSS to MPS VII mice. After 4 weeks, mice were killed, brain and liver were harvested and genomic DNA was extracted. The virus biodistribution was assessed by real-time PCR. Also, AAV-PFG-βGluc or AAV-WT-βGluc ($10 \times 10^{12}$ gp/ml) was injected into the mice through tail vein. Six weeks later, the serum was isolated and analysis of β-glucuronidase activity by fluorescent substrate assay was performed. The results showed that enzyme delivered to brain was also reaching the periphery.

Materials and Methods:

Experimental animals: MPS VII (B6.C-H-$2^{bm1}$/byBir-gus$^{mps}$/+) mice and heterozygous controls were obtained from the Jackson Laboratory (Bar Harbor, Me.), and subsequently bred and maintained at the University of Iowa animal facility. TPP1-deficient (CLN2−/−) mice have been described previously. All animal maintenance conditions and experimental protocols were approved by the University Of Iowa Animal Care and Use Committee.

In vivo biopanning: MPS VII and wild type mice (6-8 weeks of age) were each injected through the tail vein with $2\times10^{10}$ pfu of phage from the Ph.D.™-7 phage display library (New England Biolabs®, Ipswich, Mass.) in 200 μl DMEM (Invitrogen™, Carlsbad, Calif.) through the tail vein. After incubation for five minutes, the mice were anesthetized and perfused transcardially with DMEM. The brain was then extracted, and the binding phage was recovered and amplified. The amplified phage was then purified, titered, and re-injected in each of five consecutive rounds of panning. The selected phage and phage control (no inserted peptide) were amplified individually. The original Ph.D.™-7 phage display library was used as unselected control. The input phage was kept at $2\times10^{10}$ pfu/mice in each round. After the fifth round of panning, DNA from 20 randomly selected phage clones was sequenced with the primer-96gIII (New England Biolabs®, Ipswich, Mass.).

Construction of peptide modified AAV2 capsids: The plasmid for cloning of modified capsids was developed from pXX2, containing the wild-type AAV2 Rep and Cap. A plasmid with a DNA fragment encoding amino acids AAAstopA and the restriction sites NotI and AscI inserted between AAV2 Cap amino acid position 587 and 588 was constructed as the backbone plasmid. dsDNA inserts encoding selected peptides were cloned into NotI and AscI site as peptide modified pXX2.

AAV2 production and titer: Plates of 293T cells were cotransfected with three plasmids: pXX2 or peptide modified pXX2, which supplied the Rep and Cap proteins of AAV2; pHelper, which contained the adenovirus helper functions; and a vector plasmid, which contained the AAV2 ITRs and the transgene of interest. Twenty 150 mm-diameter plates were cotransfected 90 μg DNA of plasmids pXX2, pHelper, and vector at a molar ratio of 1:1:1. After incubating for 60 hours, the virus was purified with iodixanol gradients and further purification through a mustang Q membrane. Titers of recombinant AAV were determined by real-time PCR.

In vitro heparin binding assay: Viral particles ($1.0\times10^{10}$ genome particles) were bound to 50 μl of heparin agarose in 1 ml phosphate-buffered saline containing 1 mM $MgCl_2$ and 2.5 mM KCl (PBS-MK) for 2 hr at 4° C. with gentle mixing. This was then washed three times with 1 ml PBS-MK and then eluted with 30 μl PBS-MK containing 2M NaCl with vigorous vortexing. Eluted samples were analyzed by western blot with anti-AAV antibody.

In vivo biodistribution of virus: 6 to 8 weeks-old MPS VII and age-matched wildtype control mice were injected intravenously with $1.0\times10^{11}$ genome particles of wild type AAV2 or peptide modified AAV2 (PM-AAV) via the tail vein (n=3 mice per experimental group). At 4 weeks post-injection, mice were sacrificed and tissues were harvested and snap frozen. Genomic DNA from representative organs was extracted using a Qiagen® DNA extraction kit. AAV copies in a particular organ were determined by real-time PCR.

In situ enzyme activity assay: Mice injected with AAV were anesthetized and transcardially perfused with ice-cold 2% paraformaldehyde 4 weeks post-injection. Brains were harvested, embedded in OCT compound, and sectioned (16 μm) on a cryostat. Sections were washed in 0.05M NaOAC, pH 4.5 at 4° C.×10 min, incubated in 0.25 mM naphthol-SD-BI-β-D-glucuronide in 0.05M NaOAC at 37° C.×40 min, and then stained at 37°×2-4 hrs with 0.25 mM naphthol-SD-BI-β-D-glucuronide in 0.05M NaOAc buffer, pH5.2 with 1/500 2% hexazotized pararosaniline. Sections were counterstained with 0.5% methyl green solution.

MPS VII Histology: Mice were transcardially perfused with 2% paraformaldehyde and 2% glutaraldehyde in PBS, then post-fixed in the same fixative at 4° C. overnight. Tissues were blocked, fixed in 2.5% glutaraldehyde for 1 hour at room temperature and then post fixed in 1% $OsO_4$ for 2 hours at room temperature. Samples were then dehydrated and embedded in Epon™ compound. 1 μm thick sections were stained with toluidine blue solution and analyzed for cell morphology using an Olympus BX-51 Digital Light Microscope.

TPP1 Immunostaining: Mice were deeply anesthetized with intraperitoneal ketamine (100-125 mg/kg) and xylazine (10-12.5 mg/kg), then transcardially perfused with normal saline (20 mL) followed by 4% paraformaldehyde in normal saline (20 mL). Brains were then extracted and post-fixed in 4% paraformaldehyde for 24 hours at 4° C. 40 μm thick sections were cut on a freezing microtome and collected free floating in cryoprotectant solution (30% ethylene glycol, 15% sucrose, 0.05% sodium azide, in TBS) for storage at −20° C. Free floating sections were immunostained with anti-TPP1 primary antibody (Abcam) diluted in TBS with 2% BSA, 0.1% $NaN_3$, and 0.05% Tween 20. After incubation with primary antibody overnight at 4° C., tissue sections were rinsed with TBS and incubated with biotinylated goat anti-mouse secondary antibody (Jackson). Stains were developed with DAB peroxidase substrate kit (Vector Laboratories).

Context fear conditioning: The experiments were performed as previously described (Liu, G. et al., *J Neurosci* 25, 9321-7 (2005)). Six weeks after intravenous injection with $1\times10^{12}$ genome particles of virus, mice (n=6 per group) were subjected to testing in a fear-conditioning chamber (Med Association, San Diego, Calif.). Briefly, after 3 min of acclimation to the testing chamber (context 1), each mouse received seven successive electrical foot shocks (2 min apart, 0.75 mA, 50 Hz, 1 sec duration). Fear response was determined by measuring the amount of freezing behavior, which was defined as the lack of any movement other than respiratory activity. Freezing in the first 3 min after placement into the chamber was recorded during the training and again 24 h later in two contexts. Context 1 was the one used for training. Context 2 was a modified chamber with new olfactory, tactile, and visual cues. Animals stayed in their home cages during the 2 h interval between tests in the two contexts.

Analysis of PM-AAV binding site: Mouse brain vasculature was isolated by centrifuging crude brain homogenate in 15% Dextran, and further purified by running through 105 and 70 μm meshes. The vasculature separated by the 70 μm mesh were used. 50 mg of brain vasculature was incubated with PBS alone, PNGase (100 U/reaction), or chondroitinase ABC (2 U/reaction) at 37° C.×1 hr. The reaction was stopped by adding cold PBS and washed 3 times. The treated vasculatures were then incubated with virus ($1.0\times10^{11}$) in 500 μl PBS with 0.1% BSA at 4° C.×1 hr. After washing, the DNA was isolated and viral genomic particles were analyzed by real time PCR. For competitive binding of AAV-PFG to brain vasculature of MPS VII mice, 50 mg of brain vasculatures were incubated with AAV-PFG ($1.0\times10^{11}$) in the presence or absence of 2 mg/ml chondroitin sulfate at 4° C.×1 hr.

Statistical analysis: All data are expressed as means±standard deviation. An unpaired student t-test was applied to test for statistical differences. Data were considered significant when p<0.05.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A modified adeno-associated virus (AAV) capsid protein comprising a targeting peptide, wherein the targeting peptide is from 3 to 10 amino acids in length and wherein the targeting peptide targets an AAV to brain vascular endothelium, wherein the targeting peptide is GMNAFRA (SEQ ID NO:41), as expressed in an amino to carboxy orientation or in a carboxy to amino orientation.

2. The capsid protein of claim 1, wherein the targeting peptide targets a diseased brain vascular endothelium.

3. The capsid protein of claim 2, wherein the target peptide targets brain vascular endothelium in a subject that has a lysosomal storage disease.

4. The capsid protein of claim 2, wherein the targeting peptide targets TPP1-deficient-brain vascular endothelium.

5. The capsid protein of claim 1, wherein the AAV is AAV2.

6. An AAV virus containing the capsid protein of claim 1.

7. A method to deliver an agent to the central nervous system of a subject, comprising administering the virus of claim 6 to the subject.

8. The method of claim 7, wherein the AAV is AAV2.

9. The AAV virus of claim 6, wherein the AAV is AAV2.

* * * * *

UNITED STATES PATENT AND TRADEMARK OFFICE
CERTIFICATE OF CORRECTION

| | |
|---|---|
| PATENT NO. | : 8,299,215 B2 |
| APPLICATION NO. | : 12/172121 |
| DATED | : October 30, 2012 |
| INVENTOR(S) | : Davidson et al. |

It is certified that error appears in the above-identified patent and that said Letters Patent is hereby corrected as shown below:

In the Specification

In Column 1, Line 12, in the Federal Grant Support clause, please amend the second paragraph.

Replace:

"Portions of the present invention were made with support of the United States Government via a grant from the National Institutes of Health under grant number HD33531. The government has certain rights to this invention."

With:

"This invention was made with government support under HD33531, awarded by the National Institutes of Health. The government has certain rights in the invention."

Signed and Sealed this
Eighteenth Day of February, 2014

Michelle K. Lee
*Deputy Director of the United States Patent and Trademark Office*

SEQUENCE LISTING

```
<160> NUMBER OF SEQ ID NOS: 45

<210> SEQ ID NO 1
<211> LENGTH: 5
<212> TYPE: PRT
<213> ORGANISM: Artificial Sequence
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (3)
<223> OTHER INFORMATION: Any amino acid
<220> FEATURE:
<223> OTHER INFORMATION: Description of Artificial Sequence: Synthetic
      peptide

<400> SEQUENCE: 1

Pro Xaa Xaa Pro Ser
  1               5

<210> SEQ ID NO 2
<211> LENGTH: 5
<212> TYPE: PRT
<213> ORGANISM: Artificial Sequence
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (4)
<223> OTHER INFORMATION: Any amino acid
<220> FEATURE:
<223> OTHER INFORMATION: Description of Artificial Sequence: Synthetic
      peptide

<400> SEQUENCE: 2

Ser Pro Xaa Xaa Pro
  1               5

<210> SEQ ID NO 3
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Thr Leu His
  1

<210> SEQ ID NO 4
<211> LENGTH: 4
<212> TYPE: PRT
<213> ORGANISM: Artificial Sequence
<220> FEATURE:
<221> NAME/KEY: MOD_RES
<222> LOCATION: (3)
<223> OTHER INFORMATION: Any amino acid
<220> FEATURE:
<223> OTHER INFORMATION: Description of Artificial Sequence: Synthetic
      peptide

<400> SEQUENCE: 4

Gln Ser Xaa Tyr
  1

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Tyr Phe Pro Ser Leu Ser
  1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ala Pro Leu Thr Pro Ser
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Leu Ser Pro Ser Ala Tyr
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Asp Ser Pro Ala His Pro Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Thr Pro Thr His Pro Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Asp Ala Pro Ser Asn His
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Glu Pro His Trp Pro Ser
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Pro Pro Leu Pro Pro Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Pro Lys Pro Pro Pro Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic

```
        peptide

<400> SEQUENCE: 14

Asn Trp Ser Pro Trp Asp Pro
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ser Pro Ala His Pro Ser
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Trp Thr Leu His Asn Lys
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ile Pro Pro Thr Leu His
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Ser Gln Thr Leu His Gly
  1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Phe Tyr Ile Leu Thr
  1               5

<210> SEQ ID NO 20
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Thr Gln Ser Glu Tyr Gly
 1               5

<210> SEQ ID NO 21
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: Any amino acid
<220> FEATURE:
<223> OTHER INFORMATION: Description of Artificial Sequence: Synthetic
      peptide

<400> SEQUENCE: 21

Leu Xaa Ser Ser
 1

<210> SEQ ID NO 22
<211> LENGTH: 4
<212> TYPE: PRT
<213> ORGANISM: Artificial Sequence
<220> FEATURE:
<221> NAME/KEY: MOD_RES
<222> LOCATION: (3)
<223> OTHER INFORMATION: Any amino acid
<220> FEATURE:
<223> OTHER INFORMATION: Description of Artificial Sequence: Synthetic
      peptide

<400> SEQUENCE: 22

Pro Phe Xaa Gly
 1

<210> SEQ ID NO 23
<211> LENGTH: 4
<212> TYPE: PRT
<213> ORGANISM: Artificial Sequence
<220> FEATURE:
<221> NAME/KEY: MOD_RES
<222> LOCATION: (3)
<223> OTHER INFORMATION: Any amino acid
<220> FEATURE:
<223> OTHER INFORMATION: Description of Artificial Sequence: Synthetic
      peptide

<400> SEQUENCE: 23

Ser Ile Xaa Ala
 1

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Leu Val Ser Ser Pro Ala
 1               5
```

```
<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Pro Ser Ser Leu Gln Lys
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Pro Leu Leu Lys Ser Ser
  1               5

<210> SEQ ID NO 27
<211> LENGTH: 7
<212> TYPE: PRT
<213> ORGANISM: Artificial Sequence
<220> FEATURE:
<221> NAME/KEY: MOD_RES
<222> LOCATION: (2)
<223> OTHER INFORMATION: Any amino acid
<220> FEATURE:
<223> OTHER INFORMATION: Description of Artificial Sequence: Synthetic
      peptide

<400> SEQUENCE: 27

Pro Xaa Lys Leu Asp Ser Ser
  1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Trp Thr Leu Ala Ser Ser
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Pro Phe Tyr Gly Thr Pro
  1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 30

Gly Thr Phe Pro Phe Leu Gly
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gln Val Pro Phe Met Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Asn Phe Ser Ile Leu Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ser Ile Trp Ala Pro Ala
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Ile Ala Ala Ser Phe Ser
1               5

<210> SEQ ID NO 35
<211> LENGTH: 747
<212> TYPE: PRT
<213> ORGANISM: Adeno-associated virus 2

<400> SEQUENCE: 35

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45

```
Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480
```

```
Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Arg Gly Asn Ala Ala Ala Trp Pro
            580                 585                 590

Phe Tyr Gly Thr Pro Ala Ala Arg Gln Ala Ala Thr Ala Asp Val Asn
        595                 600                 605

Thr Gln Gly Val Leu Pro Gly Met Val Trp Gln Asp Arg Asp Val Tyr
    610                 615                 620

Leu Gln Gly Pro Ile Trp Ala Lys Ile Pro His Thr Asp Gly His Phe
625                 630                 635                 640

His Pro Ser Pro Leu Met Gly Gly Phe Gly Leu Lys His Pro Pro Pro
                645                 650                 655

Gln Ile Leu Ile Lys Asn Thr Pro Val Pro Ala Asn Pro Ser Thr Thr
            660                 665                 670

Phe Ser Ala Ala Lys Phe Ala Ser Phe Ile Thr Gln Tyr Ser Thr Gly
        675                 680                 685

Gln Val Ser Val Glu Ile Glu Trp Glu Leu Gln Lys Glu Asn Ser Lys
    690                 695                 700

Arg Trp Asn Pro Glu Ile Gln Tyr Thr Ser Asn Tyr Asn Lys Ser Val
705                 710                 715                 720

Asn Val Asp Phe Thr Val Asp Thr Asn Gly Val Tyr Ser Glu Pro Arg
                725                 730                 735

Pro Ile Gly Thr Arg Tyr Leu Thr Arg Asn Leu
            740                 745

<210> SEQ ID NO 36
<211> LENGTH: 18
<212> TYPE: DNA
<213> ORGANISM: Artificial Sequence
<220> FEATURE:
<221> NAME/KEY: CDS
<222> LOCATION: (1)..(18)
<220> FEATURE:
<223> OTHER INFORMATION: Description of Artificial Sequence: Synthetic
      oligonucleotide

<400> SEQUENCE: 36 aga ggc aac aga caa gca                                             18
Arg Gly Asn Arg Gln Ala
 1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Arg Gly Asn Arg Gln Ala
  1               5
```

<210> SEQ ID NO 38
<211> LENGTH: 33
<212> TYPE: DNA
<213> ORGANISM: Artificial Sequence
<220> FEATURE:
<221> NAME/KEY: CDS
<222> LOCATION: (1)..(18)
<220> FEATURE:
<221> NAME/KEY: CDS
<222> LOCATION: (22)..(33)
<220> FEATURE:
<223> OTHER INFORMATION: Description of Artificial Sequence: Synthetic
      oligonucleotide

<400> SEQUENCE: 38

```
aga ggc aac gcg gcc gcc tag gcg cgc caa gca                33
Arg Gly Asn Ala Ala Ala     Ala Arg Gln Ala
  1               5               10
```

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Arg Gly Asn Ala Ala Ala
  1               5
```

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Any amino acid

<400> SEQUENCE: 40

```
Arg Gly Asn Ala Ala Ala Xaa Ala Ala Arg Gln Asn
  1               5               10
```

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Gly Met Asn Ala Phe Arg Ala
  1               5
```

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 42

Gly Tyr Glu Ser Gln Thr Thr
  1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Arg Phe Ala Asn Met Gly
  1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Ala Ala Ala Ala
  1               5

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Arg Gln Ala
  1
```